United States Patent
Bates (10) Patent No.: US 6,220,748 B1
(45) Date of Patent: Apr. 24, 2001

(54) METHOD AND APPARATUS FOR TESTING MATERIAL UTILIZING DIFFERENTIAL TEMPERATURE MEASUREMENTS

(75) Inventor: Calvin Bates, Monroeville, PA (US)

(73) Assignee: Alcoa Inc., Pittsburgh, PA (US)

( * ) Notice: Subject to any disclaimer, the term of this patent is extended or adjusted under 35 U.S.C. 154(b) by 0 days.

(21) Appl. No.: 09/231,141

(22) Filed: Jan. 15, 1999

(51) Int. Cl.$^7$ .............................. G01N 25/00; G01K 1/00
(52) U.S. Cl. ............................................. 374/10; 374/140
(58) Field of Search ............................ 374/10, 11, 12, 374/13, 157, 140, 139, 179, 45, 161

(56) References Cited

U.S. PATENT DOCUMENTS

| | | | |
|---|---|---|---|
| 3,283,560 | * 11/1966 | Harden et al. | 374/12 |
| 3,298,220 | * 1/1967 | Stone et al. | 374/13 |
| 3,524,340 | * 8/1970 | Krakovetsky-Kocherzhinsky et al. | 374/13 |
| 3,717,034 | * 2/1973 | Dukelow et al. | 73/343 R |
| 3,818,762 | 6/1974 | Kraus et al. | 73/359 |
| 4,355,907 | 10/1982 | Orths et al. | 374/26 |
| 4,401,389 | 8/1983 | Theuwis | 374/140 |
| 4,778,281 | 10/1988 | Falk | 374/140 |
| 4,842,418 | 6/1989 | Conti | 374/139 |
| 4,893,516 | 1/1990 | Knevels | 73/866.5 |
| 5,033,320 | 7/1991 | Baerts | 73/864.59 |
| 5,209,571 | 5/1993 | Kendall | 374/139 |
| 5,332,449 | 7/1994 | Verstreken et al. | 136/234 |
| 5,388,908 | 2/1995 | Kendall | 374/140 |
| 5,415,052 | 5/1995 | Baerts | 73/864.55 |
| 5,421,215 | 6/1995 | Cure et al. | 73/864.53 |
| 5,435,196 | 7/1995 | Cassidy | 73/863.11 |
| 5,515,739 | 5/1996 | Baerts | 73/864.55 |
| 5,518,931 | 5/1996 | Plessers | 436/52 |
| 5,549,387 | * 8/1996 | Schawe et al. | 374/10 |
| 5,577,841 | 11/1996 | Wall | 374/140 |
| 5,584,578 | 12/1996 | Clauss, Jr. | 374/140 |
| 5,711,604 | * 1/1998 | Nakamura | 374/12 |
| 5,730,198 | 3/1998 | Sircar | 164/4.1 |
| 5,839,830 | * 11/1998 | Young et al. | 374/161 |

FOREIGN PATENT DOCUMENTS

| | | | |
|---|---|---|---|
| 0033961 | * 8/1981 | (EP) | 374/12 |
| 1324982 | 7/1973 | (GB) | G01N/25/48 |
| 1324983 | 7/1973 | (GB) | G01N/25/48 |
| 0255649 | * 10/1988 | (JP) | 374/10 |
| 0238828 | * 3/1969 | (SU) | 374/10 |

OTHER PUBLICATIONS

Fisher Instrument Manufacturing Division, Bulletin 10–560, Mar. 1966.*

Heraeus Brochure, "Bath and Liquidus Temperature Measurement System For the Aluminium Industry"; Jan. 1998.

* cited by examiner

Primary Examiner—G. Bradley Bennett
Assistant Examiner—Gail Verbitsky
(74) Attorney, Agent, or Firm—Alan G. Towner; Gary P. Topolosky (57) ABSTRACT

A method and apparatus for timely and accurate measurement of material parameters are disclosed. A test sensor measures the temperature of a sample of material as it is heated up and/or cooled down. A reference sensor is used to obtain differential temperature measurements as the temperature of the test sample is varied. A differential temperature trace is generated and analyzed in order to determine various characteristics of the material being tested. In one embodiment, the sodium fluoride to aluminum fluoride ratio ($NaF:AlF_3$) and alumina concentration in a Hall bath aluminum smelting operation are determined in order to efficiently control smelting of aluminum metal. In this embodiment, bath temperature and liquidus temperature may be measured and compared in order to determine the amount of superheat of the bath and to prevent the operation of smelters at higher temperatures than necessary.

12 Claims, 11 Drawing Sheets

METHOD AND APPARATUS FOR TESTING MATERIAL UTILIZING DIFFERENTIAL TEMPERATURE MEASUREMENTS

FIELD OF THE INVENTION

The present invention relates to testing of materials, and more particularly relates to a method and apparatus which utilize differential temperature measurements to determine characteristics of a material, such as the alumina concentration and sodium fluoride to aluminum fluoride ratio of an aluminum smelting bath.

BACKGROUND INFORMATION

Aluminum is conventionally produced by smelting in a Hall bath. During the smelting operation, it is desirable to control parameters such as the temperature of the bath and to determine the composition of the molten aluminum in the bath. However, the methods that are currently used to measure the alumina concentration and sodium fluoride to aluminum fluoride ratio ($NaF:AlF_3$) of the bath are confined to laboratory batch tests. Such laboratory testing causes control measurements to be made several hours after sampling, with little indication of current process conditions.

A probe that measures the bath and liquidus temperatures of a Hall bath during processing has been developed by Heraeus Electro-Nite, and is commercially available under the designation Cry-O-Therm. The probe includes a single thermocouple that is submerged in the molten bath. The Cry-O-Therm vibrates the sample during cooling to cause nucleation of the bath during cooling. An abrupt change in the slope of the cooling curve while the sample is being vibrated is taken as the liquidus. The difference between the pot temperature and the liquidus is taken as the super heat of the bath. However, this type of probe does not measure the $NaF:AlF_3$ ratio, which is critical for accurately determining the liquidus and alumina concentration.

The present invention has been developed in view of the foregoing and to address other deficiencies of the prior art.

SUMMARY OF THE INVENTION

A method and apparatus for timely and accurate measurement of material parameters are provided. A test sensor measures the temperature of a sample of material as it is heated up and/or cooled down. A reference sensor is used to obtain differential temperature measurements as the temperature of the test sample is varied. A differential temperature trace is generated and analyzed in order to determine various characteristics of the material being tested. In one embodiment, the sodium fluoride to aluminum fluoride ratio ($NaF:AlF_3$) and alumina concentration in a Hall bath aluminum smelting operation are determined in order to efficiently control smelting of aluminum metal. In this embodiment, bath temperature and liquidus temperature may be measured and compared in order to determine the amount of superheat of the bath and to prevent the operation of smelters at higher temperatures than necessary.

An aspect of the present invention is to provide a method of testing a molten material. The method includes the steps of contacting the molten material with a reference sensor and a test sensor, removing the reference and test sensors from the molten material, measuring a temperature difference between the reference and test sensors as the sensors cool down, and determining at least one characteristic of the material based on the differential temperature measurement.

Another aspect of the present invention is to provide a material testing probe comprising a support member, a reference material carried by the support member, a reference material temperature sensor in communication with the reference material, a test sample container supported by the support member, a test sample temperature sensor carried by the support member and an analyzer which determines the temperature difference between the reference material and the test material.

These and other aspects of the present invention will be more apparent from the following description.

DETAILED DESCRIPTION

The system of the present invention utilizes differential temperature measurements to determine characteristics such as the composition of a material. For example, during aluminum smelting operations, the ratio of certain constituents in the bath, e.g., $NaF:AlF_3$ ratio, and the alumina ($Al_2O_3$) concentration may be determined. While the testing of molten aluminum is primarily discussed herein, it is to be understood that the testing of other liquidus and/or solid materials is also contemplated by the present invention.

Figure 1:
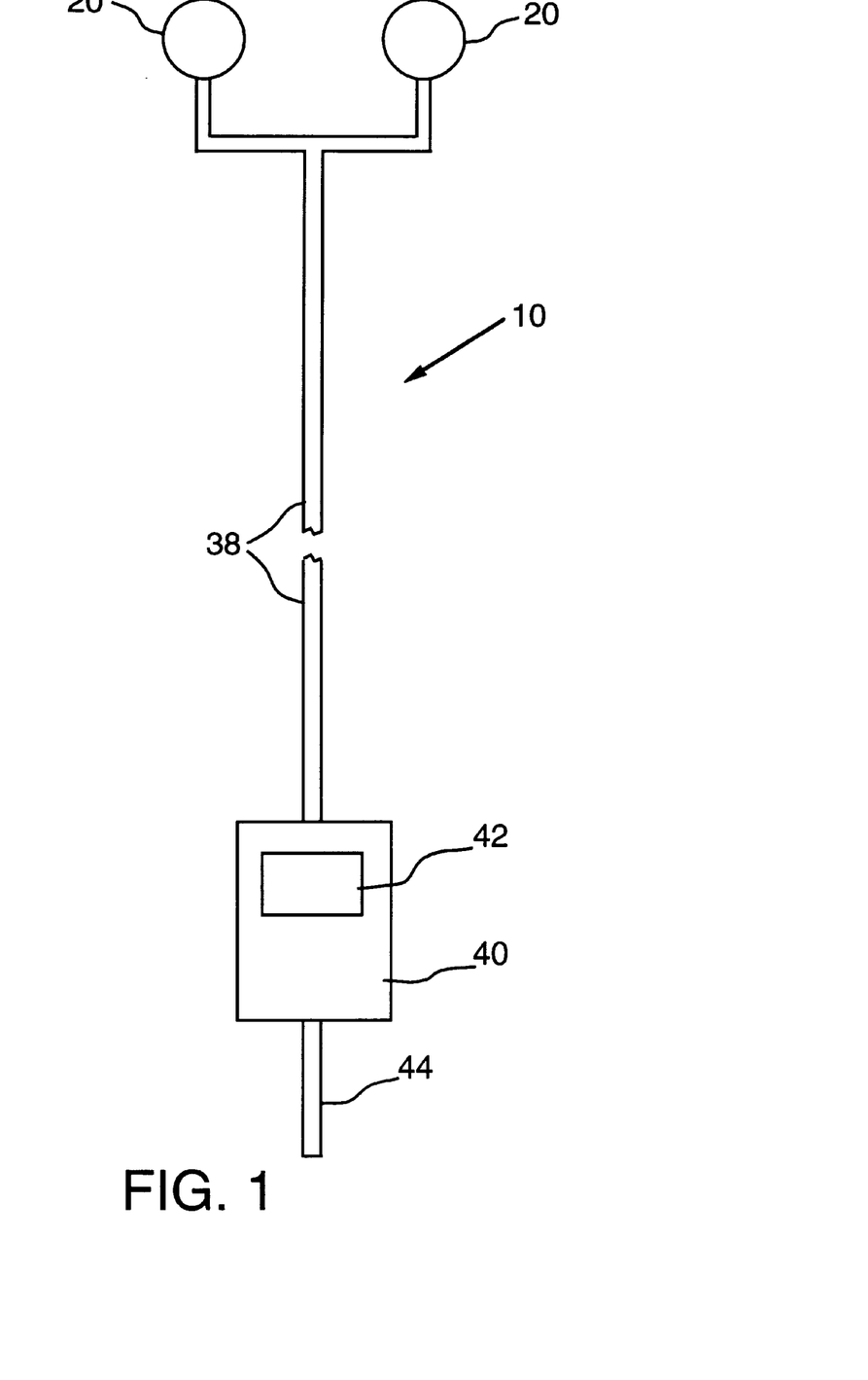
FIG. 1 is a partially schematic plan view of an aluminum smelting probe in accordance with an embodiment of the present invention.

FIG. 1 illustrates a test probe 10 in accordance with an embodiment of the present invention. The probe 10 includes a reference sensor 20 and a test sensor 30 connected to one end of a conduit 38. An analyzer 40 is positioned at the opposite end of the conduit 38, and is electrically connected to the reference sensor 20 and test sensor 30. In the embodiment shown in FIG. 1, the analyzer 40 includes a display 42 which shows information obtained from the reference sensor 20 and test sensor 30. A handle 44 is connected to the conduit 38 in order to facilitate placement of the reference sensor 20 and test sensor 30 in the desired testing location.

Figure 2:
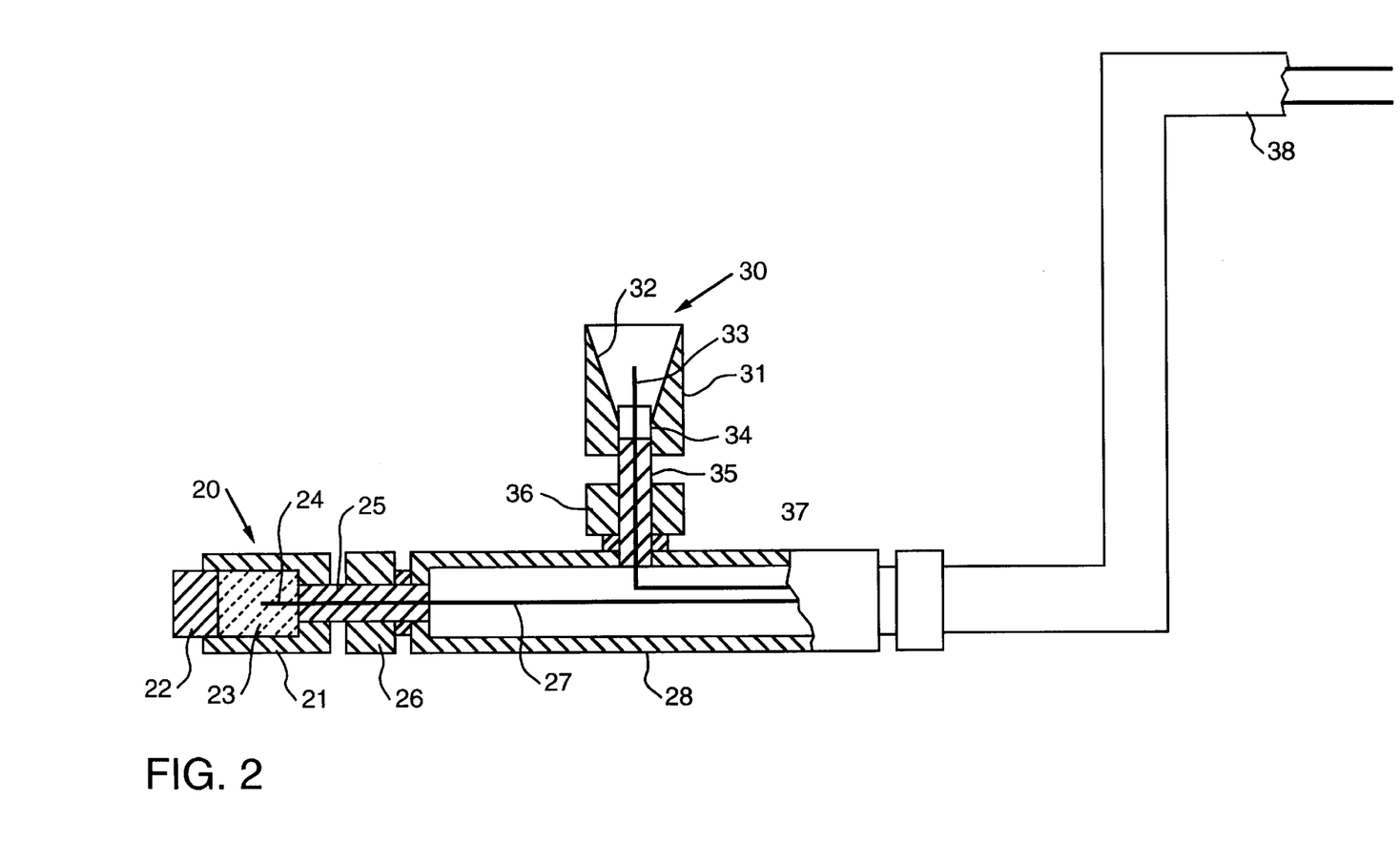
FIG. 2 is a partially schematic sectional side view of a portion of an aluminum smelting probe in accordance with an embodiment of the present invention.
Figure 3:
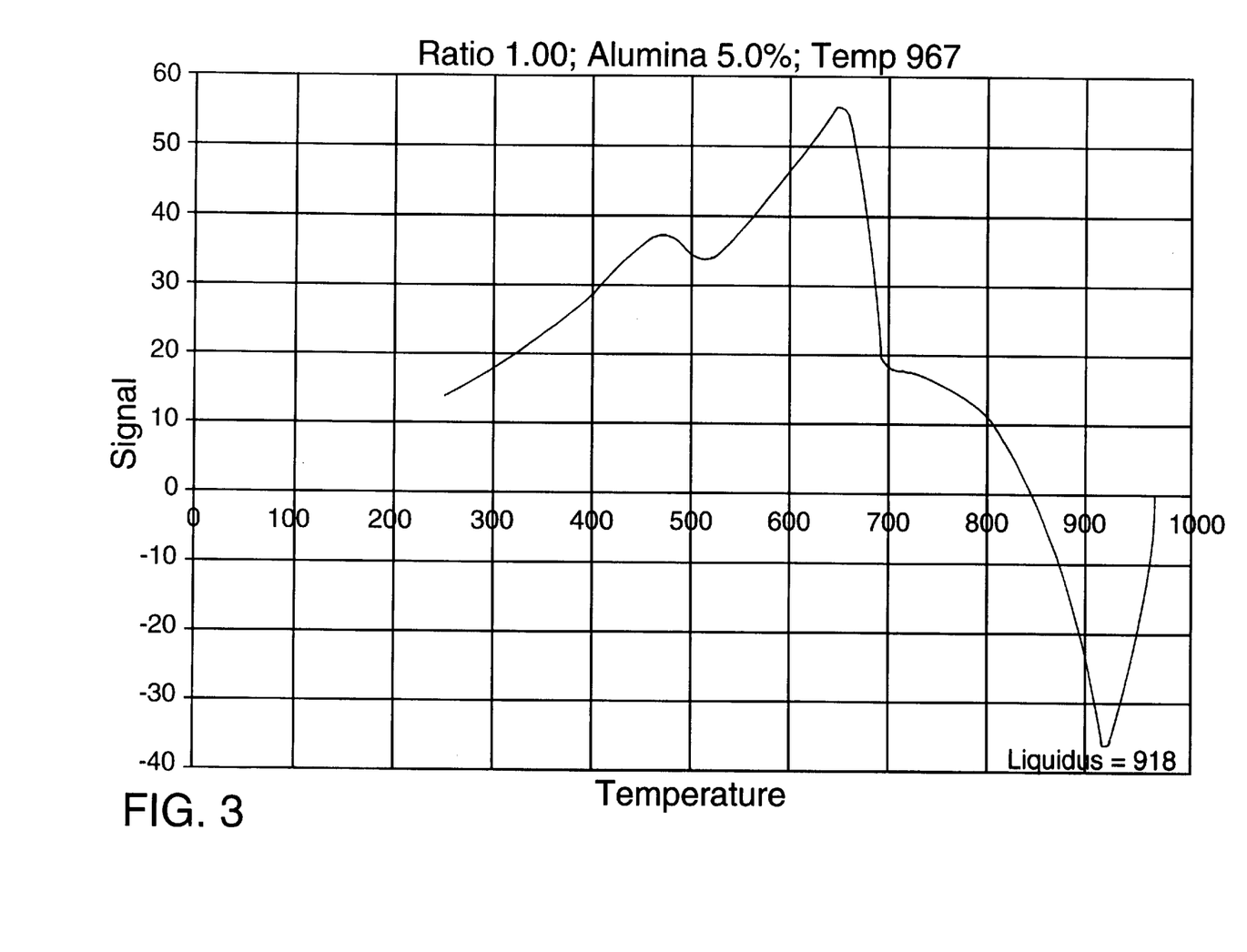
FIGS. 3–8 are graphs of differential temperature signals versus time for aluminum smelting baths having different $NaF:AlF_3$ ratios, showing increases in liquidus temperatures for test samples having higher $NaF:AlF_3$ ratios.
Figure 4:
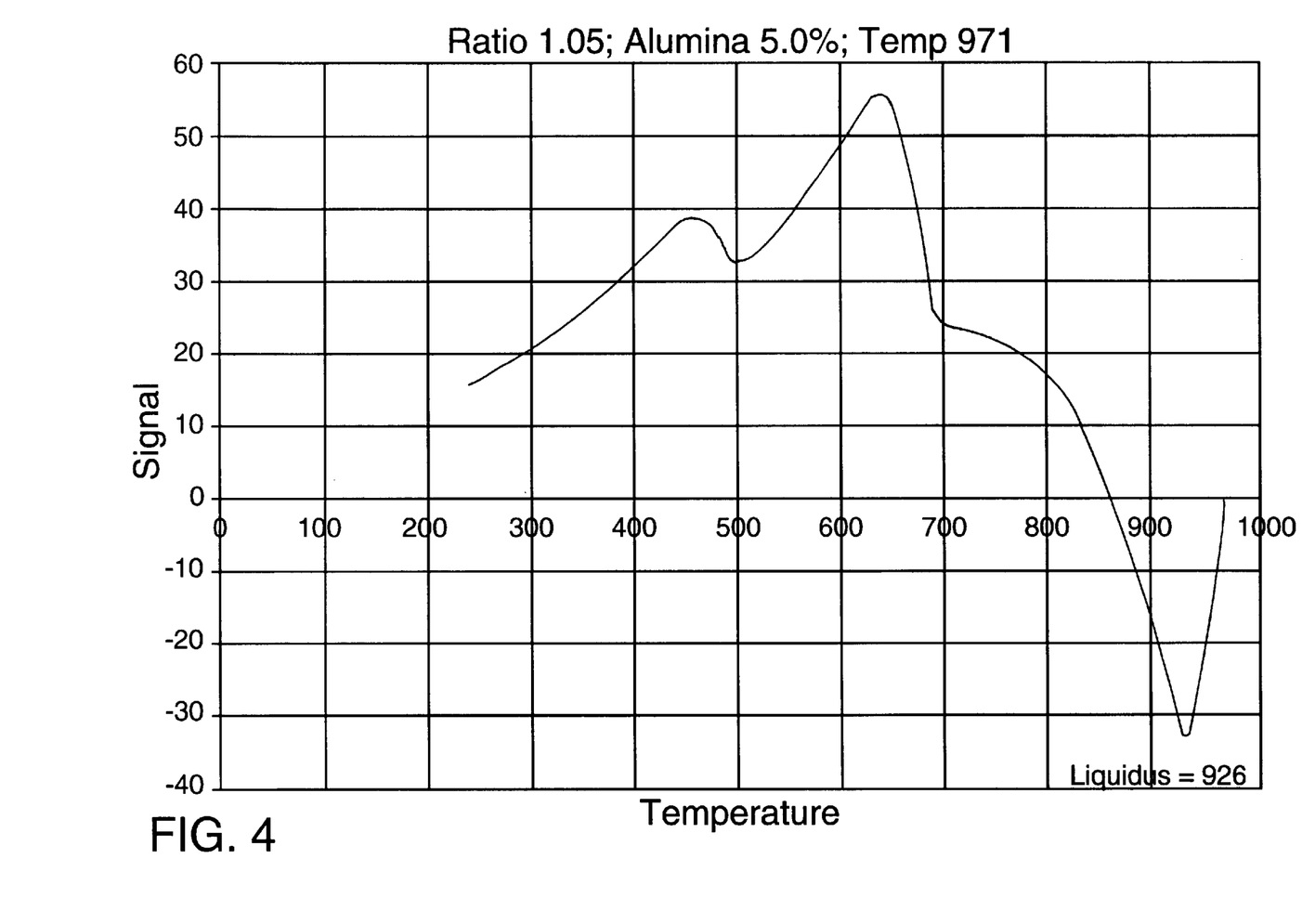
Figure 5:
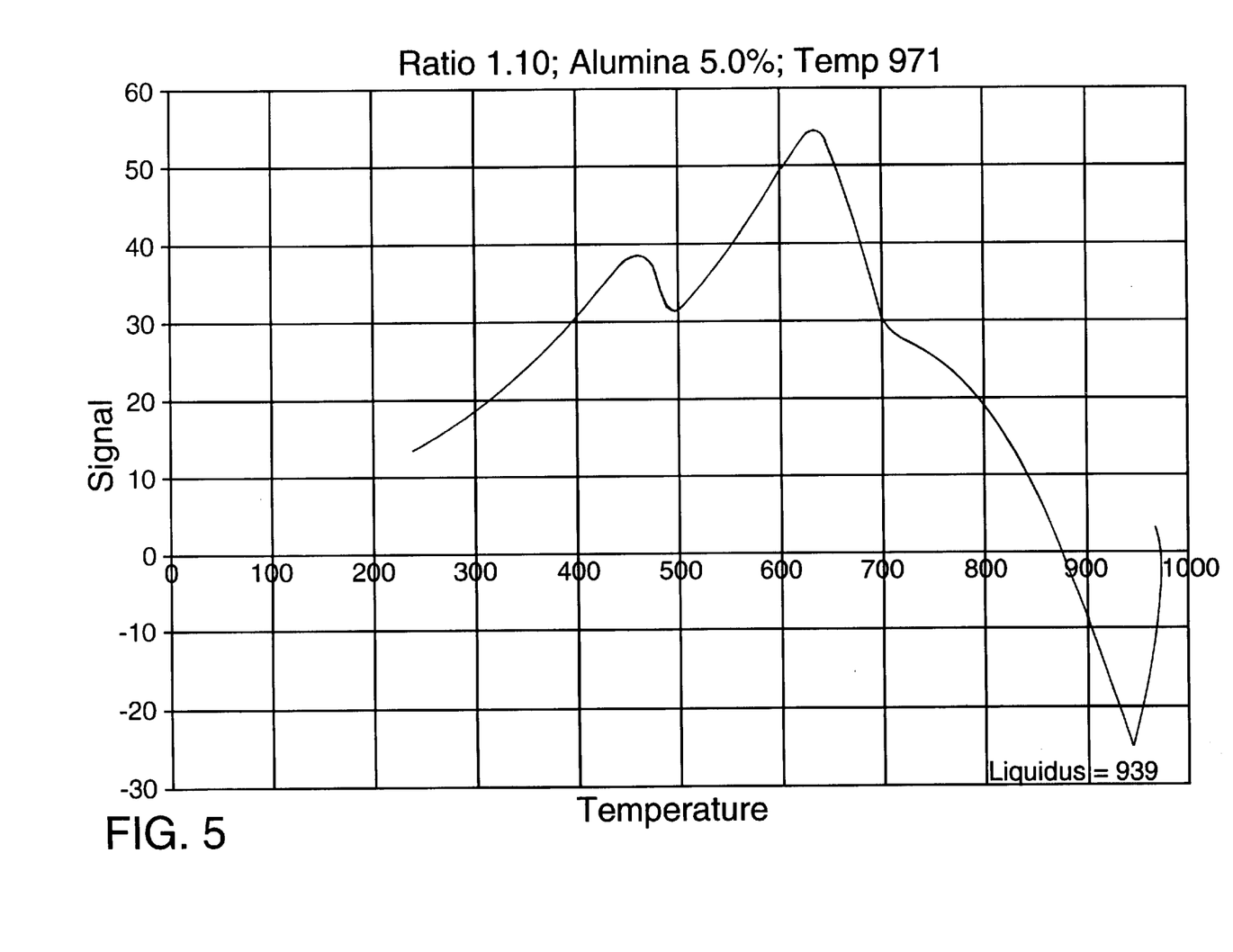
Figure 6:
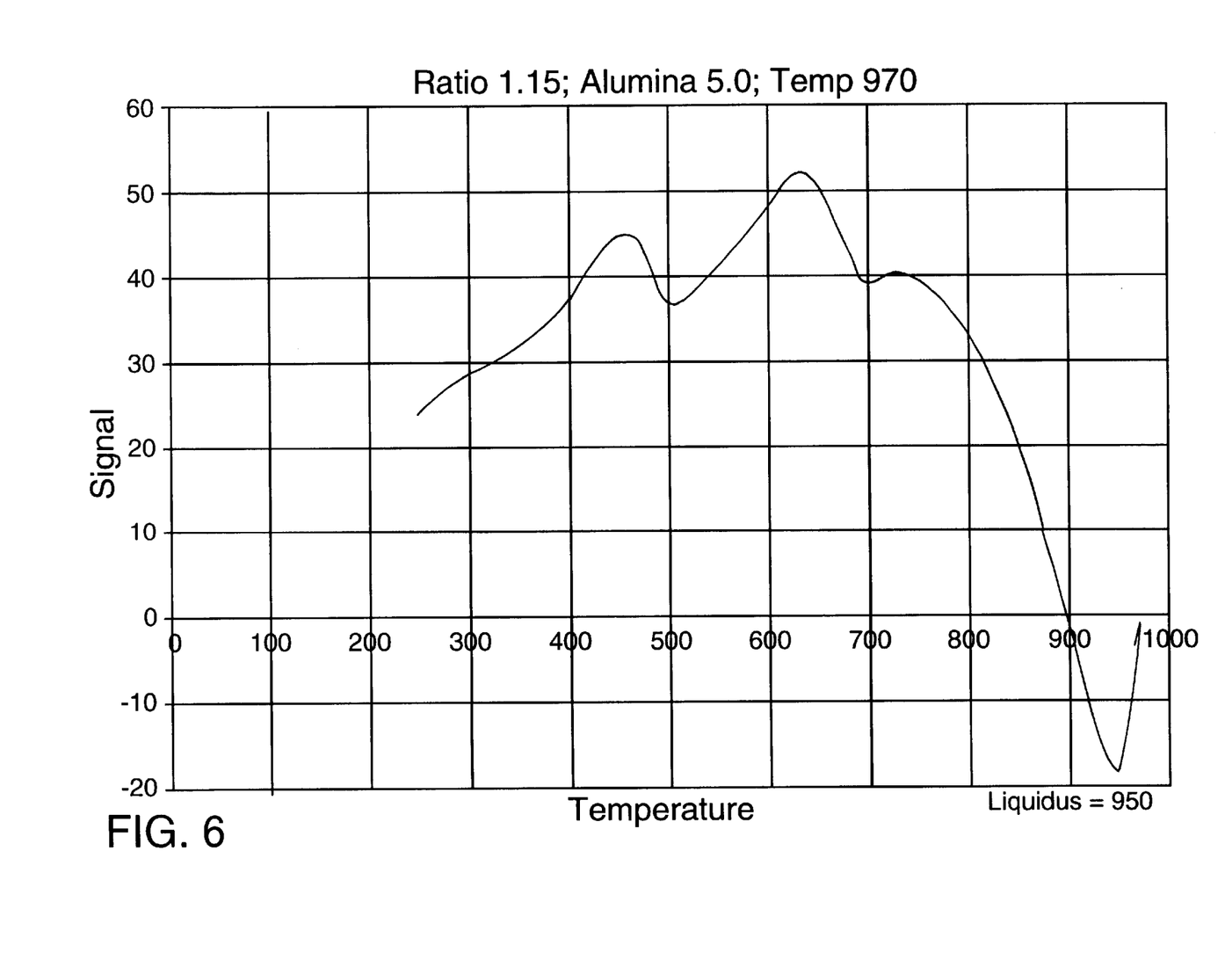
Figure 7:
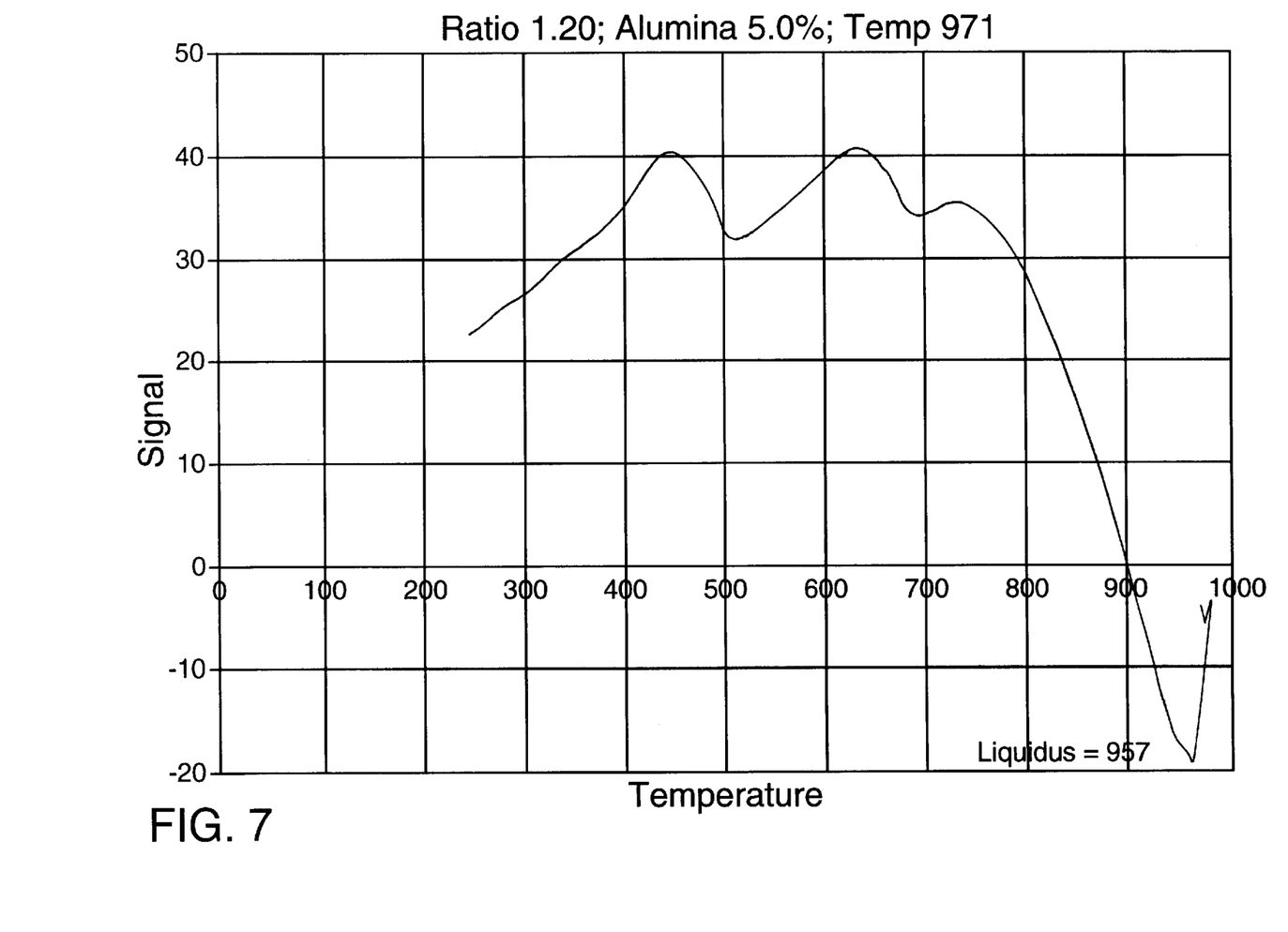
Figure 8:
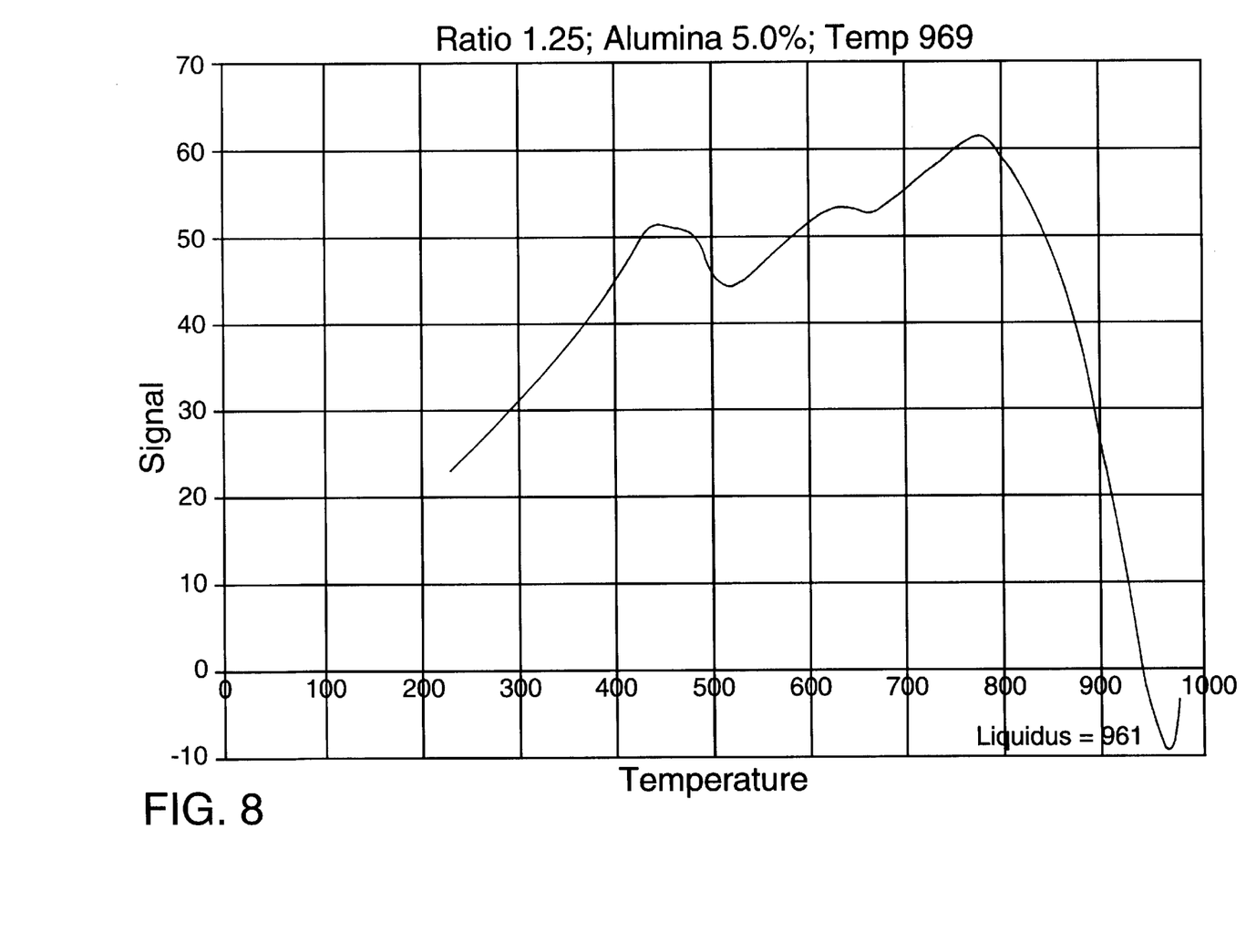

FIG. 2 illustrates a portion of a probe in accordance with an embodiment of the present invention. The reference sensor 20 which is located at one end of the probe, includes a housing 21 and a cap 22 defining a generally cylindrical chamber. A reference material 23 is provided inside the chamber formed by the housing 21 and cap 22. The reference material 23 may be any suitable material from which a temperature reading may be obtained and compared with a temperature reading from a test sample, as more fully described below. The reference material 23 is preferably provided in the form of a solid material in the temperature ranges to be tested. However, liquid and/or gaseous reference materials may also be used. The reference material 23 preferably does not undergo a phase transformation in the testing temperature range in order to provide a substantially constant baseline temperature readings throughout the testing procedure. Suitable reference materials include metals, ceramics, calcined alumina and refractories. For example, the reference material 23 may comprise a metal such as 1199 aluminum, stainless steel or refractory metals. Furthermore, the reference material 23 may comprise a ceramic such as metal grade alumina (MGA). For testing aluminum smelting baths, metal grade alumina is particularly preferred.

As shown in FIG. 2, a reference thermocouple 24 extends into the housing 21 in contact with the reference material 23. A refractory fitting 25 extends through a wall of the housing 21 and surrounds an electrical lead 27 of the reference thermocouple 24. The refractory fitting 25 extends through a connecting collar 26 which is fastened to a hollow support member 28.

In the embodiment shown in FIG. 2, the test sensor 30 is generally cup-shaped and includes a housing 31 defining a substantially conical interior test chamber 32. A test thermocouple 33 extends into the test chamber 32. The test thermocouple 33 is secured to the housing 31 by means of cement 34 and a refractory fitting 35. The refractory fitting 35 extends through a connecting collar 36 mounted on the hollow support member 28. A test thermocouple lead 37 extends through the cement 34 and refractory fitting 35 into the interior of the support member 28. The reference thermocouple lead 27 and the test thermocouple lead 37 extend from the interior of the support member 28 into the conduit 38 and are preferably connected to an analyzer 40, as shown in FIG. 1. The conduit 38 may be any suitable length. For example, where the probe 10 is used for testing aluminum smelting baths, the conduit 38 may be preferably from about 0.5 to about 10 feet in length.

The various components of the probe are made of any suitable materials. For example, the housings 21 and 31, cap 22, connecting collars 26 and 36, support member 28 and conduit 38 may be made of metal such as stainless steel, inconel, monel or aluminum. The refractory fittings 25 and 35 may be made of fiberfrax rope, or the like. The cement 34 may be, for example, a mixture of graphite, solvent and binder sold under the designation C34 that has been cured to a temperature of about 150° C.

In accordance with an embodiment of the present invention, the probe sensors 20 and 30 may be submerged into a molten bath with the configuration shown in FIG. 2 in which the test sensor 30 is an open cup being open to collect a sample and measure the temperature of the molten bath. The reference sensor 20 is closed and contains smelting grade alumina 23, or another thermally inert material, which acts as a stable reference material. After a stable pot temperature is noted, the probe sensors 20 and 30 are removed from the bath with the open cup filled with molten metal. The test and reference samples are then cooled, e.g., to 250° C., via ambient air, convection or other means. Convection cooling is particularly preferred for many testing operations in order to expedite the test process. During the cooling process, the difference in temperature between the test sample and the reference sample is recorded as delta temperature ($\Delta T$), for example, using a meter comprising a conventional voltage amplification board and data logger. The profile obtained from this configuration is a plot of microvolts versus temperature and/or time. The thermal arrests indicated by peaks and valleys are indicative of the formation of different phases forming as the sample cools, as more fully described below.

In accordance with an embodiment of the present invention, it has been observed that in an aluminum smelting bath sample, the magnitude of the differential temperature transition at approximately 400 to 500° C. is directly correlated to $NaF:AlF_3$ ratio, with constant alumina concentration. Furthermore, with varying alumina concentrations, the ratio of $NaF:AlF_3$ in cryolite may be correlated to another differential temperature peak, between about 600 and 800° C., in the cooling profile (transition/thermal arrest). Also, the differential temperature profile shows the liquidus or temperature at which the bath begins to freeze by means of a first minimum point of the differential temperature trace during cooling. This first minimum or valley of the differential temperature trace typically occurs at a temperature greater than 900° C. In addition, the probe may be used to measure the temperature of the smelting bath, and the amount of superheat of the bath may be determined by subtracting the liquidus temperature from the bath temperature. The present system thus allows the calculation of parameters such as alumina concentration, $NaF:AlF_3$ ratio and superheat.

The following examples illustrate various aspects of the present invention, and are not intended to limit the scope thereof.

EXAMPLE 1

A probe similar to that shown in FIGS. 1 and 2 is used to measure a series of aluminum smelting baths. In each bath, the alumina concentration is held constant at about 5.0 weight percent while the $NaF:AlF_3$ ratio is varied from 1.00 to 1.25 in increments of 0.05. During the testing procedure each bath is held at a temperature above the expected liquids temperature. A sample of Hall Cell Bath was obtained. The sodium Fluoride to Aluminum Fluoride ratio was determined via X-ray diffraction and pyrotitration methods. The amount of alumina was determined via a LECO oxygen analyzer. The ratio of the sample was 1.14 and the alumina concentration was 3.97 percent. The bulk of the sample was placed in a crucible furnace and melted under a nitrogen atmosphere. Sodium fluoride and or Aluminum Fluoride was added to the melt to adjust the ratio up or down in the range of 1.0 to 1.25. Smelting or metal grade alumina was added to as needed to adjust the alumina from the 3.97 percent starting point up to 6.0 percent. After adjusting the ratio and/or the alumina concentration to the desired level, a DTA probe was submerged in the bath. The probe remained submerged in the bath until a stable temperature was measured by the probe and a full cup of the bath was captured. Upon measuring a stable temperature the bath filled cup of the probe was removed from the melt and air cooled to at least 400°. The DTA profile was recorded as the sample cooled. Differential temperature profiles are shown in FIGS. 3-8 for each of the test runs. In each run, when the reference sample and test sample are simultaneously removed from the bath, the difference in temperature between the reference sample and the test sample is plotted as the samples cool from the molten bath temperature to a temperature of about 250° C. Each differential temperature trace includes an initial valley which indicates the liquidus temperature of the test sample, i.e., the temperature at which the molten sample begins to freeze. The following table lists the liquidus temperature for each test sample in comparison with the $NaF:AlF_3$ ratio for each sample.

TABLE 1

| $NaF:AlF_3$ | Liquidus Temp. (° C.) |
|---|---|
| 1.00 | 918 |
| 1.05 | 926 |
| 1.10 | 939 |

TABLE 1-continued

| NaF:AlF$_3$ | Liquidus Temp. (° C.) |
|---|---|
| 1.15 | 950 |
| 1.20 | 957 |
| 1.25 | 961 |

As can be seen from Table 1 and FIGS. 3–8, as the NaF:AlF$_3$ ratio increases from a value of 1.00 to a value of 1.25, the liquidus temperature, as measured by the differential temperature valley, increases from 918 to 961° C. Based upon this demonstrated relationship between liquidus temperature and NaF:AlF$_3$ ratio for the various test samples, the probe of the present invention may be calibrated to determine and display the NaF:AlF$_3$ ratio for a particular test sample.

EXAMPLE 2

Figure 9:
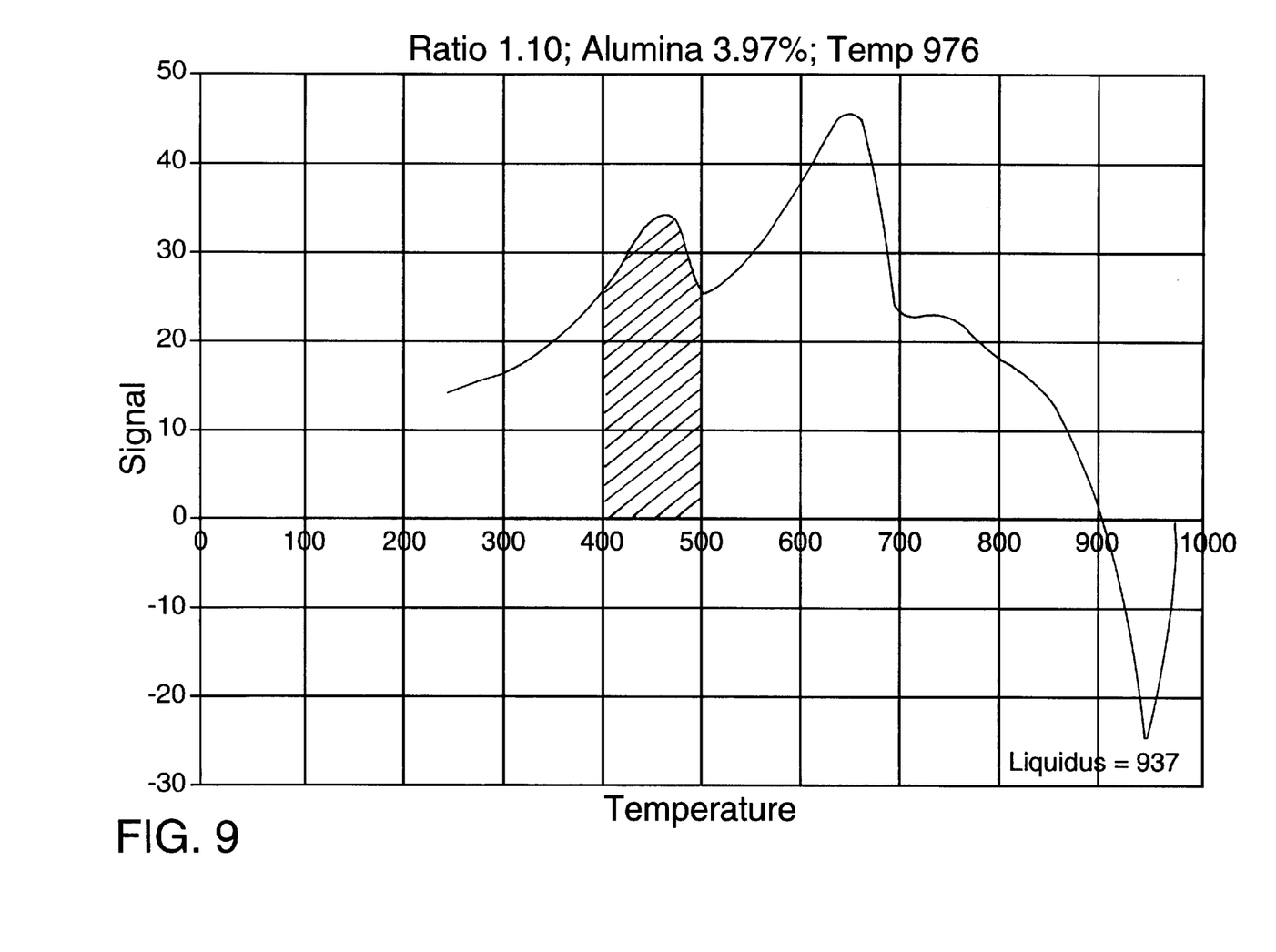
FIGS. 9–11 are graphs of differential temperature signals versus time for aluminum smelting baths having different alumina concentrations, showing differences in the integrated area under a portion of each curve for test samples having different alumina concentrations.
Figure 10:
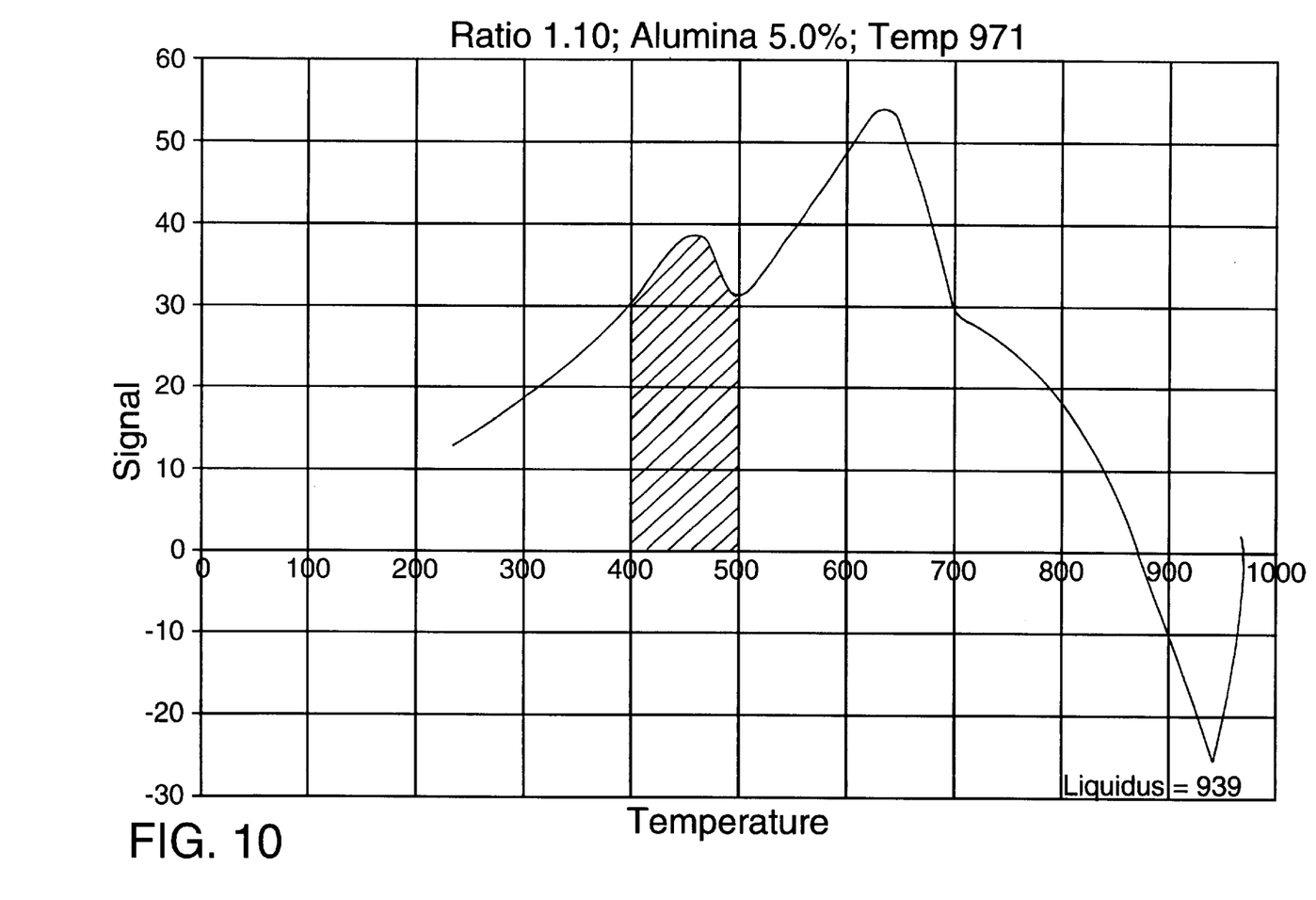
Figure 11:
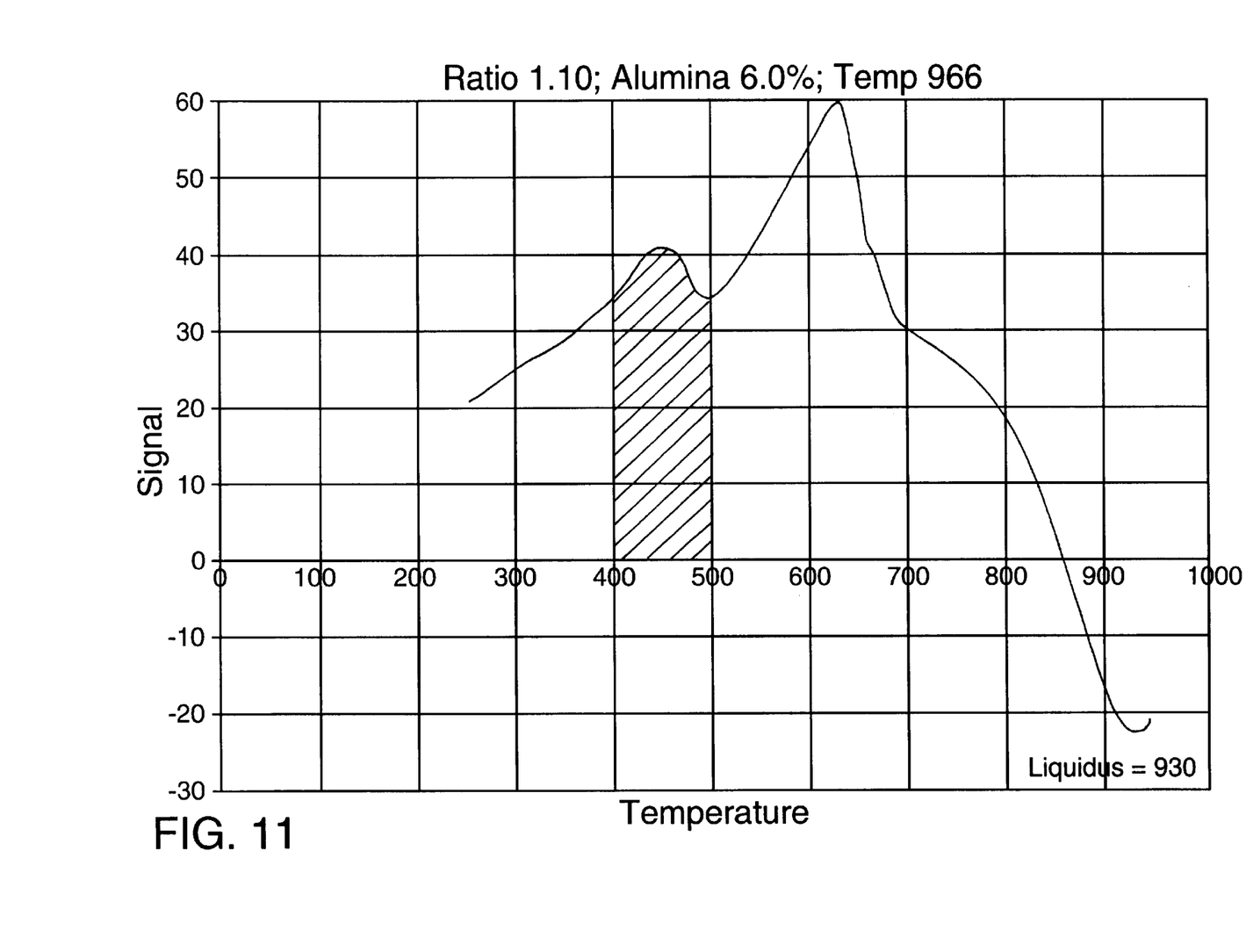

A probe similar to that shown in FIGS. 1 and 2 is used to measure a series of aluminum smelting baths. In each bath, the NaF:AlF$_3$ ratio is held constant at a value of 1.10, while the alumina concentration is varied from 3.97 to 6.0 weight percent. During the testing procedure, each bath is held at a substantially constant temperature of 971±5° C. Differential temperature profiles are shown in FIGS. 9–11 for each of the test runs. As shown in FIGS. 9–11, after each differential temperature trace goes through an initial valley, the differential temperature signal becomes positive and yields a trace having several peaks as the sample cools down. For example, in each trace, a differential temperature peak occurs within the temperature range of from about 600 to about 700° C. Another temperature peak occurs in each trace between about 400 and 500° C. In accordance with the present invention, such differential temperature peaks can be used to determine the alumina concentration of each test sample. For example, as shown by the cross-hatched regions of FIGS. 9–11, the differential temperature trace may be integrated between 400 and 500° C. to provide a value indicative of the alumina concentration of each sample. In FIG. 9, an alumina concentration of 3.97 weight percent yields an integrated value of –5264. In FIG. 10, an alumina concentration of 5.0 weight percent yields an integrated value of –4800. In FIG. 11, an alumina concentration of 6.0 weight percent yields an integrated value of –4231. It can therefore be seen that as the alumina concentration increases, the integrated differential temperature curve between 400 and 500° C. also increases. In accordance with a preferred embodiment of the present invention, this correlation may be used to calibrate the test probe in order to directly analyze and display the alumina concentration of a test sample. Other regions of the differential temperature traces may also be analyzed in accordance with the present invention. For example, the differential temperature peak appearing between 600 and 700° C. in FIGS. 9–11 may be integrated or otherwise analyzed to determine alumina concentration or the like. Also the overall appearance of the pro files can be used to tack Hall Cell Chemistry during production.

In addition to measuring the NaF:AlF$_3$ ratio and alumina concentration in aluminum test samples, the probe of the present invention may also be used to measure other parameters. For example, the probe may measure the pot temperature of the aluminum smelting bath while the probe is submersed therein. Thus, the reference sensor 20 and/or test sensor 30 shown in FIGS. 1 and 2 may be used to directly measure the pot temperature. Furthermore, the probe may be used to determine the superheat or overtemperature of the bath by determining the liquidus temperature of a test sample and then subtracting that value from the measured pot temperature.

The present invention thus provides the ability to measure parameters such as pot temperature, bath ratio and alumina concentration on a real-time basis for improved process control, thereby resulting in increased efficiency of aluminum production. Also, the present system lessens the need for laboratory measurements for alumina and NaF:AlF$_3$ ratio in samples taken from the process.

The method and apparatus of the present invention may be used to test other types of materials. For example, other types of molten metals may be analyzed. Furthermore, the system of the present invention may be used to test solid materials such as metals undergoing heat treatment or refractory materials undergoing curing processes. As a particular example, phase transitions may be monitored in aluminum alloys during the heat treatment thereof. In this embodiment, the test sensor contacts the aluminum alloy during the heat treatment process. The reference sensor preferably includes a reference material that does not undergo a phase transformation in the measured heat treatment temperature range. An example of a suitable reference material is 1199 aluminum.

In this embodiment, the reference material is preferably sized so as to simulate an infinitely large heat transfer element. The differential temperature measurements may be made as the aluminum alloy heats up during the heat treatment temperature regime. Typically, as the aluminum alloy heats up, the differential temperature trace hits a positive peak indicative of precipitation and then hits a negative valley indicative of dissolution. Thereafter, the differential temperature trace rises and levels off, indicating the occurrence of solubility equilibrium.

For many aluminum alloys, once solubility equilibrium occurs, as indicated by the leveling off of the differential temperature trace, the purpose of the heat treatment process has effectively been achieved. However, in conventional heat treatment processes, it is not possible to accurately determine the exact time at which solubility equilibrium is substantially completed. Accordingly, standard heat treatment processing times are often used which are longer than necessary to achieve the desired heat treatment results. In accordance with this embodiment of the present invention, shortened heat treatment processing times are possible because the completion of solubility may be accurately determined. Processing costs may therefore be substantially reduced by decreasing both time and energy requirements for heat treatment operations.

Whereas particular embodiments of this invention have been described above for purposes of illustration, it will be evident to those skilled in the art that numerous variations of the details of the present invention may be made without departing from the invention as defined in the appended claims.

What is claimed is:

1. A method of testing a molten material comprising:
   submersing a reference sensor and a test sensor in the molten material;
   removing the reference and test sensors from the molten material;
   measuring a temperature difference between the reference and test sensors as the sensors cool down; and
   determining a NaF:AlF$_3$ ratio of the molten material based on the differential temperature measurement.

2. The method of claim 1, wherein the molten material comprises aluminum.

3. The method of claim 2, further comprising providing the molten material in an aluminum smelting bath.

4. The method of claim 3, further comprising determining a liquidus of the molten material based on the differential temperature measurement.

5. The method of claim 3, further comprising determining an alumina concentration of the molten material based on the differential temperature measurement.

6. The method of claim 1, further comprising determining a liquidus of the molten material based on the differential temperature measurement.

7. A molten material testing probe comprising:
a support member;
a reference material supported by the support member and submersible in the molten material;
a reference material temperature sensor in communication with the reference material;
a test sample container supported by the support member and submersible in the molten material;
a test sample temperature sensor supported by the support member in communication with the test sample container; and
an analyzer capable of determining a difference between the temperature measured by the reference material temperature sensor and the temperature measured by test sample temperature sensor after the sensors have been removed from the molten material, wherein the analyzer comprises means for determining a $NaF:AlF_3$ ratio of the test sample based on the temperature difference between the reference material and the test sample.

8. The molten material testing probe of claim 7, wherein the test sample container comprises an open cup defining an interior volume.

9. The molten material testing probe of claim 8, wherein the test sample temperature sensor comprises a thermocouple extending into the interior volume of the test sample container.

10. The molten material testing probe of claim 7, wherein the analyzer comprises means for determining a liquidus of a test sample contained in the test sample container based on the temperature difference between the reference material and the test sample.

11. The molten material testing probe of claim 7, wherein the test sample container holds a molten test sample comprising aluminum.

12. The molten material testing probe of claim 11, wherein the analyzer comprises means for determining an alumina concentration of the test sample based on the temperature difference between the reference material and the test sample.

* * * * *